(12) United States Patent
Saeki et al.

(10) Patent No.: US 8,071,837 B2
(45) Date of Patent: Dec. 6, 2011

(54) METHOD OF MANUFACTURING ABSORBENT ARTICLE, MANUFACTURING APPARATUS FOR ABSORBENT BODY, AND ABSORBENT ARTICLE MANUFACTURED THEREBY

(75) Inventors: Tatsuya Saeki, Tokyo (JP); Jun Kudo, Tokyo (JP)

(73) Assignee: Uni-Charm Corporation, Ehime (JP)

( * ) Notice: Subject to any disclaimer, the term of this patent is extended or adjusted under 35 U.S.C. 154(b) by 769 days.

(21) Appl. No.: 11/598,343

(22) Filed: Nov. 13, 2006

(65) Prior Publication Data

US 2007/0107571 A1    May 17, 2007

(30) Foreign Application Priority Data

Nov. 14, 2005    (JP) ................. 2005-329512

(51) Int. Cl.
*A61F 13/15* (2006.01)
(52) U.S. Cl. ............. 604/378; 604/385.101; 604/380; 604/383; 604/385.01; 604/385.17
(58) Field of Classification Search ............ 604/385.17, 604/385.101, 378, 380, 383, 385.01
See application file for complete search history.

(56) References Cited

U.S. PATENT DOCUMENTS

| | | | |
|---|---|---|---|
| 3,814,101 A * | 6/1974 | Kozak | 604/370 |
| 4,622,036 A * | 11/1986 | Goodrum | 604/367 |
| 5,397,316 A | 3/1995 | LaVon et al. | |
| 5,925,299 A | 7/1999 | Dierckes, Jr. et al. | |

FOREIGN PATENT DOCUMENTS

| | | | |
|---|---|---|---|
| EP | 0 293 208 | | 11/1988 |
| JP | H04-51930 U | | 5/1992 |
| JP | H07-024007 A | * | 1/1995 |
| JP | 9-504471 | | 5/1997 |
| JP | H10-071171 | | 3/1998 |
| JP | H10-131014 | | 5/1998 |
| JP | 2000-246687 | | 9/2000 |
| JP | D1154999 | | 10/2002 |
| JP | 2003-038552 A | * | 2/2003 |
| JP | D1169280 | | 3/2003 |
| JP | D1169425 | | 3/2003 |
| JP | D1174600 | | 6/2003 |
| JP | D1174983 | | 6/2003 |
| JP | D1175692 | | 6/2003 |
| JP | D1176343 | | 6/2003 |

(Continued)

OTHER PUBLICATIONS

Notice of Reasons for Rejection issued in corresponding Japanese Application No. 2005-329512, mailed Jun. 29, 2010.

(Continued)

*Primary Examiner* — Jacqueline F. Stephens
(74) *Attorney, Agent, or Firm* — Brinks Hofer Gilson & Lione (57) ABSTRACT

An apparatus for manufacturing an absorbent body for an absorbent article includes a conveying mechanism for conveying a continuous absorbent sheet, a slitting mechanism configured so that a plurality of slitting blades are pressed against the absorbent sheet conveyed by the conveying mechanism, the slitting blades extending in a predetermined direction, a cutting mechanism for cutting the absorbent sheet against which the slitting blades are pressed and forming the absorbent body, and a stretching mechanism arranged upstream of the cutting mechanism and for stretching, in a direction orthogonal to the predetermined direction, the absorbent sheet against which the slitting blades are pressed, and forming slits in the absorbent sheet.

8 Claims, 7 Drawing Sheets

FOREIGN PATENT DOCUMENTS

| | | |
|---|---|---|
| JP | D1176373 | 6/2003 |
| JP | D1176374 | 6/2003 |
| JP | D1196974 | 2/2004 |
| JP | D1196975 | 2/2004 |
| JP | D1197310 | 2/2004 |
| JP | D1198639 | 3/2004 |
| JP | 2004-141620 A * | 5/2004 |
| JP | 2005-095574 A * | 4/2005 |
| JP | 2005-205026 A | 8/2005 |
| JP | 2005-212149 A | 8/2005 |
| TV | 581621 | 3/2004 |
| TV | 581624 | 3/2004 |
| TW | 582957 | 4/2004 |
| WO | WO 95/10995 | 4/1995 |
| WO | WO 99/42068 | 8/1999 |
| WO | WO 2006/025934 | 3/2006 |

OTHER PUBLICATIONS

Notice of Reasons for Rejection issued in corresponding Japanese Application No. 2005-329512, mailed Mar. 1, 2011.

* cited by examiner

METHOD OF MANUFACTURING ABSORBENT ARTICLE, MANUFACTURING APPARATUS FOR ABSORBENT BODY, AND ABSORBENT ARTICLE MANUFACTURED THEREBY

This application is based on and claims the benefit of priority from Japanese Patent Application No. 2005-329512, filed on Nov. 14, 2005, the content of which is incorporated herein by reference.

BACKGROUND OF THE INVENTION

1. Field of the Invention

The present invention relates to an apparatus and method of manufacturing absorbent bodies used in absorbent articles, such as a sanitary napkin, panty liner, incontinent pad, etc., for absorbing bodily fluids such as menstrual blood, vaginal discharge, etc., and absorbent bodies manufactured thereby.

2. Related Art

Conventionally, with the aim of enhancing handling-ability, etc., there is a demand for reduction in thickness of absorbent articles, such as a sanitary napkin, panty liner, incontinent pad, etc., for absorbing bodily fluids such as menstrual blood, vaginal discharge, etc. However, if the absorbent article is made thin, there arises a problem in that an absorbent body that is a component for absorbing and maintaining bodily fluids becomes stiff and solid, impairing flexibility.

Thus, an absorbent article is disclosed, for example, in JP-A 2003-038552 (referred to hereinafter as Patent Document 1).

The absorbent article includes a liquid permeable top sheet, a liquid impermeable back sheet, and an absorbent body interposed therebetween. The absorbent article has concave and convex portions arranged continuously on both faces to extend along the length direction of the absorbent body. With this, the absorbent body has a corrugated cross-section.

With this absorbent article, since the absorbent body is formed to have a corrugate section, the distance between corrugations can be adjusted in accordance with an applied force, leading to enhanced flexibility of the absorber.

With this absorbent article, however, since the absorber is formed to have a corrugated cross-section, the adhesion area is reduced between the absorbent body and the back sheet, degrading the linkage therebetween. As a consequence, even if the back sheet follows movement of clothing by a well-known displacement preventing means, etc., the absorbent body does not move together with the back sheet, and thus cannot follow movement of the clothes sufficiently. This may cause easy twisting of the absorbent body, resulting in possible occurrence of leakage of bodily fluids.

An absorbent article is disclosed, for example in JP-U 04-051930 (referred hereinafter as Patent Document 2).

This absorbent article includes a liquid permeable top sheet, a liquid impermeable back sheet, and an absorbent body interposed therebetween. A plurality of slits are formed in the absorbent body.

With the absorbent article, due to arrangement of a plurality of slits in the absorbent body, when clothing moves, the absorbent body moves and bends together therewith, so that the projection-side external surface of a bend opens the slits, whereas the inside of the bend closes the slits. With this, the absorbent body can deform, bend, etc., while restraining occurrence of a high-stiffness part at the bend, resulting in enhancement in flexibility of the absorbent article.

Moreover, as distinct from the absorbent article disclosed in Patent Document 1, a problem that the linkage between the absorbent body and the back sheet is degraded by a reduction in adhesion area therebetween, does not easily occur.

The absorbent body having a plurality of slits is manufactured by a method using the following manufacturing apparatus.

This manufacturing apparatus includes a conveying roller for conveying a continuous absorbent sheet, a slitting roller having on the external surface a plurality of slitting blades extending in a predetermined direction and arranged so that the slitting blades are pressed against the absorbent sheet conveyed by the conveying roller, a cutting roller for cutting the absorbent sheet against which the slitting blades are pressed and forming the absorbent body for absorbent articles, and a drive motor for rotating the rollers.

The manufacturing apparatus operates as follows. First, the conveying roller is rotated by the drive motor to convey the continuous absorbent sheet. The slitting roller rotated by the drive motor presses the slitting blades against the absorbent sheet conveyed. Then, the cutting roller rotated by the drive motor cuts the absorbent sheet in a predetermined shape, manufacturing the absorbent body.

In recent years, there is an increasing demand for mass production of absorbent articles, and accordingly, high-speed conveyance of absorbent sheet is required in manufacturing processes of the absorbent bodies.

However, if high-speed conveyance of the absorbent sheet is performed using the above-mentioned manufacturing apparatus, the slitting blades are not sufficiently pressed against the absorbent sheet conveyed at high speed to penetrate the absorbent sheet, leading to cases in which slits cannot be fully formed.

Moreover, parts of the absorbent sheet in which the slitting blades do not penetrate are increased in density, having greatly increased hardness. As a consequence, the absorbent article using this absorbent body may have increased stiffness, leading to possible degradation in flexibility.

SUMMARY OF THE INVENTION

It is an object of the present invention to provide a method and apparatus for manufacturing more assuredly an absorber having slits formed therein even when performing high-speed conveyance of a continuous absorbent sheet, and an absorber manufactured thereby.

Specifically, the following are provided by the present invention.

According to a first aspect of the present invention, there is provided a method of manufacturing an absorbent body for an absorbent article, including: pressing a plurality of slitting blades against a continuous absorbent sheet, the plurality of slitting blades extending in a first direction; stretching, in a direction orthogonal to the first direction, the absorbent sheet against which the plurality of slitting blades are pressed and forming slits in the absorbent sheet; and cutting the absorbent sheet, in which the slits are formed, in a predetermined shape, and forming the absorbent body.

According to the first aspect of the present invention, there is arranged, prior to a cutting process, a process of stretching, in the direction orthogonal to a first direction, the absorbent sheet against which the plurality of slitting blades are pressed, and forming slits in the absorbent sheet. As a consequence, even if the slitting blades are not sufficiently pressed against the absorbent sheet conveyed at high speed to penetrate into the absorbent sheet, the absorbent sheet is stretched in the direction orthogonal to the direction along which the slitting blades extend, forming the slits in the absorbent sheet.

Therefore, even when high-speed conveyance of the continuous absorbent sheet is performed, the absorber, in which slits are formed, can be manufactured more surely.

It is noted that, in the specification, the wording "first direction" refers to the direction parallel to the direction of conveyance direction of the absorbent sheet, and the wording "second direction" refers to the direction orthogonal to the direction of conveyance.

Stretching the absorbent sheet in the direction orthogonal to a predetermined direction may be obtained by drawing the absorbent sheet in this direction, pressing and bending the absorbent sheet in the direction orthogonal to the surface thereof, hammering the absorbent sheet, etc.

According to a second aspect of the present invention, there is provided an apparatus for manufacturing an absorbent body for an absorbent article, including: a conveying mechanism that conveys a continuous absorbent sheet; a slitting mechanism configured so that a plurality of slitting blades are pressed against the absorbent sheet conveyed by the conveying mechanism, the plurality of slitting blades extending in a first direction; a cutting mechanism that cuts the absorbent sheet against which the plurality of slitting blades are pressed and forms the absorbent body; and a stretching mechanism arranged upstream of the cutting mechanism, the stretching mechanism stretching in a second direction orthogonal to the first direction, the absorbent sheet against which the plurality of slitting blades are pressed, and forming slits in the absorbent sheet.

According to the second aspect of the present invention, a stretching mechanism is arranged upstream of the cutting mechanism to stretch, in the second direction orthogonal to the first direction, the absorbent sheet against which the plurality of slitting blades are pressed, and forms slits in the absorbent sheet. As a consequence, even if the slitting blades are not sufficiently pressed against the absorbent sheet that are conveyed at high speed, to penetrate into the absorbent sheet, the absorbent sheet is stretched in the direction orthogonal to the direction along which the slitting blades extend, forming the slits in the absorbent sheet.

Therefore, even when high-speed conveyance of the continuous absorbent sheet is performed, the absorbent body, in which slits are formed, can be manufactured more surely.

It is noted that, in the specification, the wording "upstream" refers to the direction opposite the direction of conveyance of the absorbent sheet, and the wording "downstream" refers to the forward direction with respect to the direction of conveyance of the absorbent sheet.

According to a third aspect of the apparatus as described in the second aspect of the present invention, the first direction is parallel to a direction of conveyance of the absorbent sheet, wherein the stretching mechanism includes a plurality of rotary rollers each arranged in order on upper and lower sides of the absorbent sheet at a constant interval in the second direction, the plurality of rotary rollers each pressing and bending the absorbent sheet on a side opposite a side on which the rotary rollers are arranged, the plurality of rotary rollers stretching, in the second direction, the absorbent sheet against which the plurality of slitting blades are pressed, and forming the slits in the absorbent sheet.

According to the third aspect of the present invention, since a slitting mechanism is configured so that a plurality of slitting blades extend in the first direction parallel to the direction of conveyance, the slitting blades are pressed against the absorbent sheet, forming a pressed part that extends in the direction of conveyance.

The stretching mechanism includes a plurality of rotary rollers arranged in order on upper and lower sides of the absorbent sheet at a constant interval in the second direction orthogonal to the direction of conveyance. With this, when conveyed to pass the stretching mechanism, the absorbent sheet, having a pressed part formed therein, is pressed and bent upwardly and downwardly alternately by the respective rotary rollers, causing stretching in the second direction.

As a consequence, even if the slitting blades are not sufficiently pressed against the absorbent sheet, that is conveyed at high speed, to penetrate into the absorbent sheet, the absorbent sheet is stretched in second the direction to allow the slitting blades to penetrate into the pressed part extending in the first direction, forming the slits in the pressed part.

Therefore, even when high-speed conveyance of the continuous absorbent sheet is performed, the absorbent body, in which slits are formed, can be manufactured more surely.

According to a fourth aspect of the apparatus as described in the second aspect of the present invention, the stretching mechanism includes a plurality of rotary rollers each arranged in order on upper and lower sides of the absorbent sheet at a constant interval in the second direction, the plurality of rotary rollers including a roller having a cross-sectional shape obtained by cutting a circular arc of a predetermined angle from a circular shape, the slitting mechanism comprises a slitting roller, wherein a length of a circular arc remaining without being cut substantially corresponds to a rotation-direction length of an area of the slitting roller in which the plurality of the slitting blades are arranged.

According to a fifth aspect of the present invention, there is provided a apparatus for manufacturing an absorbent body for an absorbent article, including: a conveying mechanism that conveys a continuous absorbent sheet; a slitting mechanism configured so that a plurality of slitting blades are pressed against the absorbent sheet conveyed by the conveying mechanism, the plurality of slitting blades extending in a second direction orthogonal to a first direction that corresponds to a direction of conveyance of the absorbent sheet; a cutting mechanism that cuts the absorbent sheet, against which the plurality of slitting blades are pressed, and forms the absorbent body; and a stretching mechanism arranged upstream of the cutting mechanism, the stretching mechanism stretching, in the first direction, the absorbent sheet against which the plurality of slitting blades are pressed, and forming slits in the absorbent sheet, the stretching mechanism including at least one pair of rotary rollers each having on an external surface a plurality of projections that extend in the second direction, wherein, by the plurality of projections of the at least one pair of rotary rollers engaging with each other, the at least one pair of rotary rollers stretch in the first direction, the absorbent sheet against which the plurality of slitting blades are pressed, and form the slits.

According to the fifth aspect of the present invention, since a slitting mechanism is configured so that a plurality of slitting blades extend in the second direction orthogonal to the direction of conveyance, the slitting blades are pressed against the absorbent sheet, forming a pressed part that extends in the second direction.

The stretching mechanism includes at least one pair of rotary rollers each having on an external surface a plurality of projections that extend in the second direction. With this, when conveyed to pass through the stretching mechanism, as the plurality of projections of the pair of rotary rollers extending in the second direction engage with each other, the absorbent sheet, in which pressed parts are formed, is engaged with the engaging part, and is stretched in the first direction parallel to the direction of conveyance.

As a consequence, even if the slitting blades are not sufficiently pressed against the absorbent sheet, that is conveyed at high speed, to penetrate into the absorbent sheet, the absorbent sheet is stretched in the first direction to allow the slitting blades to penetrate into the pressed part extending in the second direction, forming the slits in the pressed part.

Therefore, even when high-speed conveyance of the continuous absorbent sheet is performed, the absorbent body, in which slits are formed, can be manufactured more assuredly.

It is noted that, in the specification, the wording "pressed part(s)" refers to an area pressed by the slitting blades, and particularly, an area into which the slitting blades did not penetrate.

According to a sixth aspect of the present invention, the stretching mechanism includes at least one pair of first rotary rollers each having on an external surface a plurality of projections that extend in the second direction, and a plurality of second rotary rollers arranged in order on upper and lower sides of the absorbent sheet a constant intervals in the second direction, wherein, by the plurality of projections of the at least one pair of first rotary rollers engaging with each other, the at least one pair of first rotary rollers stretch in the first direction, the absorbent sheet, against which the plurality of slitting blades are pressed, and form the slits, and in which the plurality of second rotary rollers press and bend the absorbent sheet on a side opposite a side in which the second rotary rollers are arranged, the plurality of second rotary rollers stretching in the second direction, the absorbent sheet against which the plurality of slitting blades are pressed, and forming the slits in the absorbent sheet.

According to the sixth aspect of the apparatus as described in the second aspect of the present invention, since a slitting mechanism is configured so that a plurality of slitting blades extend in the second direction and in the first direction, the slitting blades are pressed against the absorbent sheet, forming a pressed part that extends both in the second direction and in the first direction.

The stretching mechanism includes at least one pair of rotary rollers each having on an external surface a plurality of projections that extend in the second direction. With this, when conveyed to pass through the stretching mechanism, as the plurality of projections of the pair of rotary rollers extending in the second direction engage with each other, the absorbent sheet having pressed parts formed therein is engaged with the engaging part, and is stretched in the first direction.

Moreover, a plurality of second rotary rollers are arranged in order on upper and lower sides of the absorbent sheet at a constant interval in the second direction. With this, when conveyed to pass the stretching mechanism, the absorbent sheet having pressed part formed therein is pressed and bent upwardly and downwardly alternately by the respective rotary rollers, causing stretch in the second direction.

As a consequence, even if the slitting blades are not sufficiently pressed against the absorbent sheet, that is conveyed at high speed, to penetrate into the absorbent sheet, the absorbent sheet is stretched in the first and second directions to allow the slitting blades to penetrate into the pressed part extending in the first and second directions, forming the slits in the pressed part.

Therefore, even when high-speed conveyance of the continuous absorbent sheet is performed, the absorbent article having slits formed therein can be manufactured more assuredly.

Arrangement of the first rotary rollers and second rotary rollers in the stretching mechanism is not limited particularly. Specifically, the second rotary rollers may be arranged upstream of the first rotary rollers, or alternatively, the first rotary rollers may be arranged upstream of the second rotary rollers The absorbent article manufactured by the apparatus according to the sixth aspect of the present invention has slits formed in the two directions, providing more favorable conformity to movement of the clothes than that of the absorbent body manufactured by the apparatus according to the third or fifth aspect of the present invention.

According to a seventh aspect of the present invention, there is provided an absorbent body for an absorbent article manufactured by the apparatus according to any one of the second, third, fourth, and sixth aspects of the present invention.

According to an eighth aspect of the present invention, there is provided an absorbent body for an absorbent article manufactured by the apparatus according to the fifth aspect of the present invention.

According to the seventh and eighth aspects of the present invention, since the absorber is manufactured by the above-mentioned apparatus, the same effect as that of the above-mentioned apparatus can be obtained.

The manufacturing method of the present invention produces the following effects.

There is arranged, prior to a cutting process, a process of stretching in the second direction, the absorbent sheet against which the plurality of slitting blades are pressed, and of forming slits in the absorbent sheet. As a consequence, even if the slitting blades are not sufficiently pressed against the absorbent sheet, that is conveyed at high speed, to penetrate into the absorbent sheet, the absorbent sheet is stretched in the direction orthogonal to the direction along which the plurality of slitting blades extend, forming the slits in the absorbent sheet.

Therefore, even when high-speed conveyance of the continuous absorbent sheet is performed, the absorbent body having slits formed therein can be manufactured more surely.

The manufacturing apparatus of the present invention produces the following effects.

A stretching mechanism is arranged upstream of the cutting mechanism to stretch, in the second direction, the absorbent sheet against which the plurality of slitting blades are pressed and form slits into the absorbent sheet. As a consequence, even if the slitting blades are not sufficiently pressed against the absorbent sheet, that is conveyed at high speed, to penetrate into the absorbent sheet, the absorbent sheet is stretched in the direction orthogonal to the direction along which the slitting blades extend, forming the slits in the absorbent sheet.

Therefore, even when high-speed conveyance of the continuous absorbent sheet is performed, the absorber, in which slits are formed, can be manufactured more assuredly.

DETAILED DESCRIPTION OF THE INVENTION

Referring to the drawings, embodiments of the present invention are described hereinafter. It is noted that descriptions of the embodiments outside of the first embodiment are made giving like reference numerals to parts the same as those in the first embodiment and their description is omitted or simplified.

First Embodiment

General Configuration of the Manufacturing Apparatus

Figure 1:
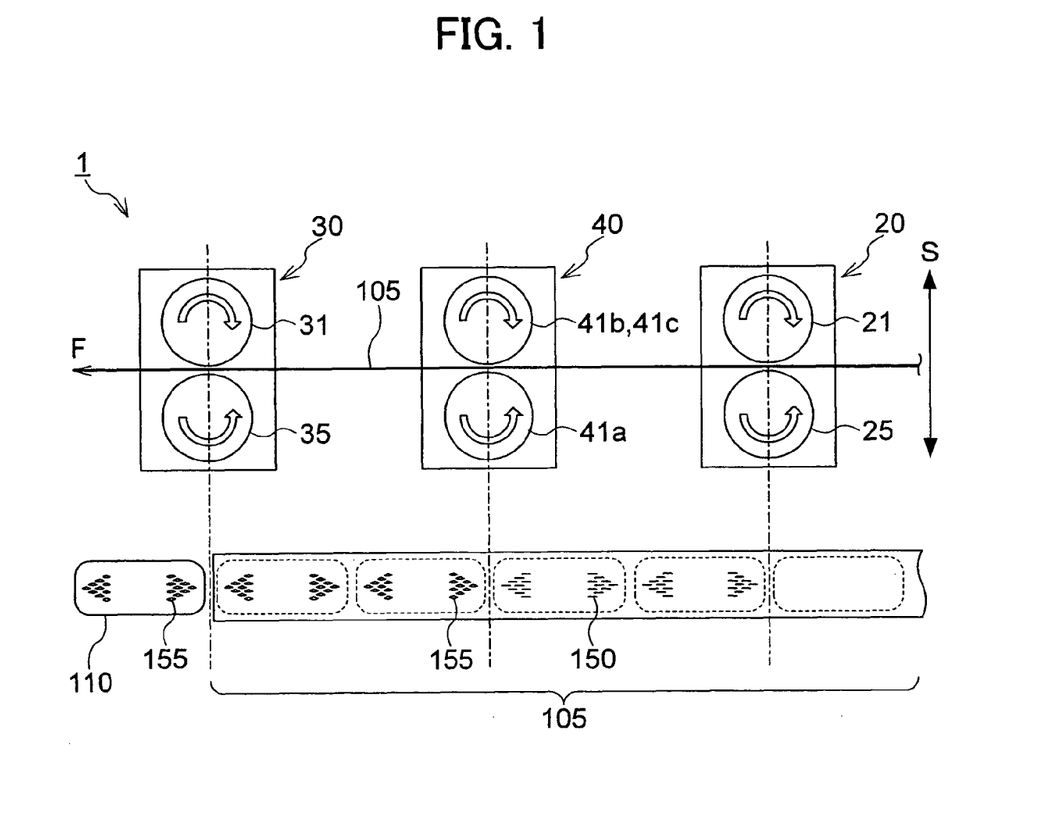
FIG. 1 is a schematic diagram showing a manufacturing apparatus according to a first embodiment of the present invention.

FIG. 1 is a schematic diagram showing a manufacturing apparatus 1 according to the first embodiment of the present invention.

Referring to FIG. 1, the manufacturing apparatus 1 includes a conveying mechanism, not shown, a slitting mechanism 20, and a cutting mechanism 30. The manufacturing apparatus 1 includes a stretching mechanism 40 arranged downstream of the slitting mechanism 20 and upstream of the cutting mechanism 30.

A continuous long absorbent sheet 105 is provided to the manufacturing apparatus 1. Rollers (as will be described later) constituting the slitting mechanism 20, cutting mechanism 30, and stretching mechanism 40 are all arranged to rotate in a first direction shown as arrow F that substantially corresponds to the direction of conveyance.

The continuous long absorbent sheet 105 has a structure in which a combination of a crushed-pulp part and an absorbent-polymer part is enveloped by a tissue. The crushed-pulp part is formed so that a 180 g/m$^2$ weight area and a 500 g/m$^2$ weight area are alternately arranged in the length direction of the absorbent sheet 105. The absorbent-polymer part has 10 g/m$^2$ weight and is formed so that the absorbent sheet 105 in its entirety becomes uniform.

The 180 g/m$^2$ weight area of the crushed-pulp part is pressed to have the surface flattened.

Conveying Mechanism

A roller, conveyor belt, etc. are mentioned as a conveying mechanism. Among them, the roller is preferably used based on the point that high-speed conveyance of the absorbent sheet 105 can be performed.

Slitting Mechanism

Figure 2:
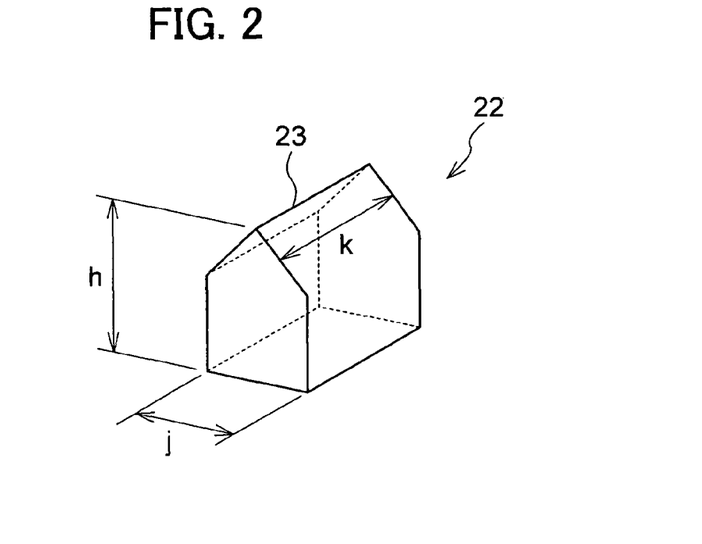
FIG. 2 is a perspective view showing the shape of a tip of a slitting blade provided to a slitting roller constituting a slitting mechanism.

FIG. 2 is a perspective view showing the shape of a tip of a slitting blade 22 provided to a slitting roller 21 constituting a slitting mechanism 20.

Referring to FIGS. 1 and 2, the slitting mechanism 20 includes a slitting roller 21, a drive motor as a slitting-roller rotating mechanism, not shown, for rotating the slitting roller 21, and a receiving-side roller 25 arranged opposite the slitting roller 21 and cooperating with the slitting roller 21 to hold the absorbent sheet 105.

The slitting roller 21 includes on part of the external surface a plurality of slitting blades 22. The slitting blades 22 are arranged so that a cutting edge 23 extends in the direction of rotation of the slitting roller 21.

The slitting blades 22 are formed to have a rectangle as a bottom in which a dimension j of a side orthogonal to the direction of rotation is 2.6 mm, a dimension k of a side parallel to the direction of rotation is 5 mm, and maximum height h is 4 mm.

Rotation of the slitting roller 21 is controlled by the drive motor so that the slitting blades 22 are pressed against the 180 g/m$^2$ weight area of the crushed-pulp part of the absorbent sheet 105.

The receiving-side roller 25 is pressed against the slitting roller 21 by a predetermined pressing force. The receiving-side roller 25 is not limited particularly, and may have a soft surface so as not to damage the cutting edge of the slitting blades 22. Moreover, the receiving-side roller 25 is rotated in synchronicity with the slitting roller 21 so as not to produce a shearing force in the slitting blades 22.

Stretching Mechanism

Figure 3:
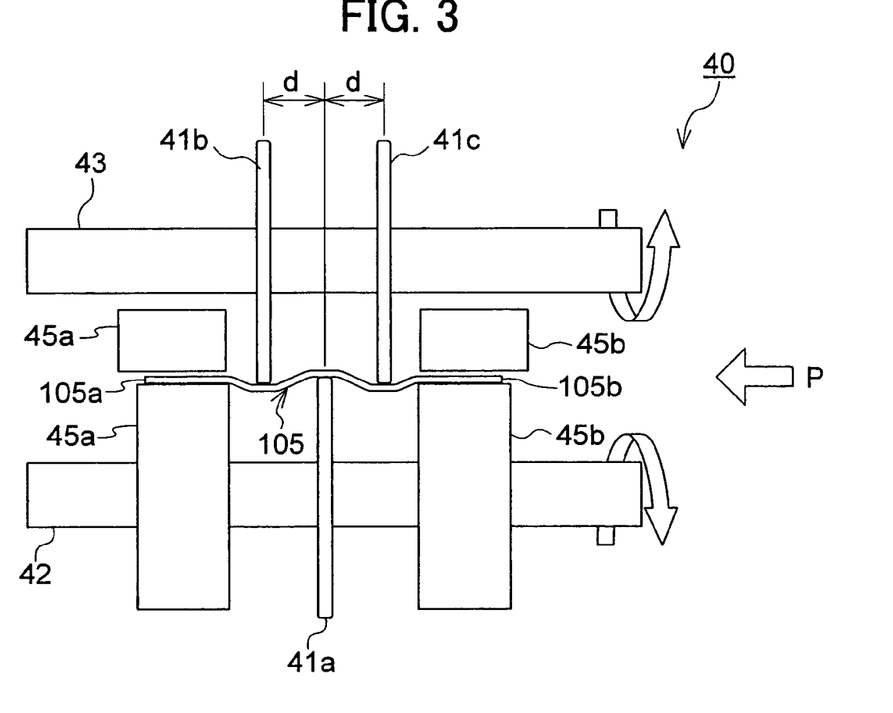
FIG. 3 is a front view showing a stretching mechanism seen from the direction of rotation.
Figure 4:
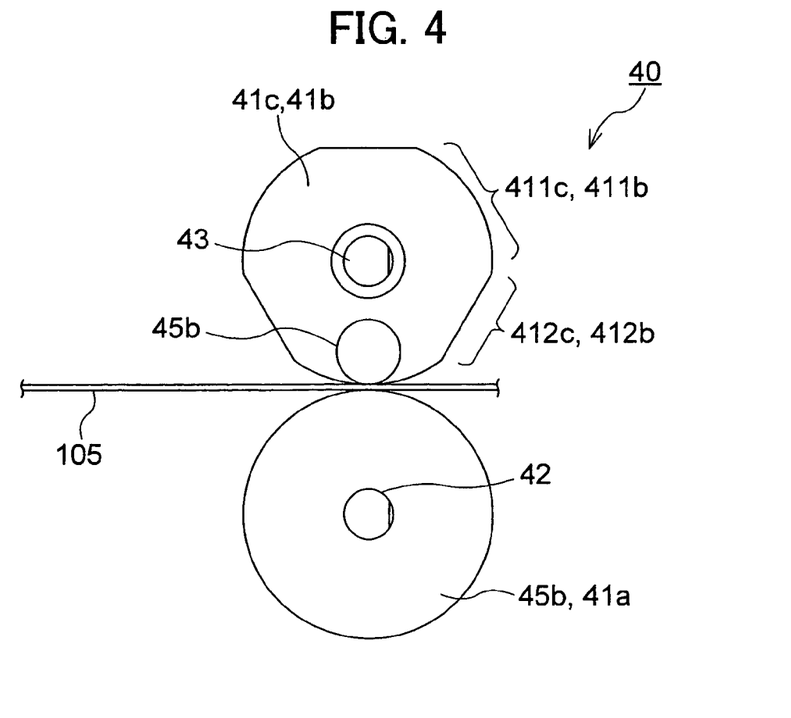
FIG. 4 is a side view showing the stretching mechanism in FIG. 3 seen from the direction of an arrow P.

FIG. 3 is a front view showing a stretching mechanism 40 seen from the direction of rotation. FIG. 4 is a side view showing the stretching mechanism 40 in FIG. 3 seen from the direction of an arrow P.

Referring to FIGS. 3 and 4, the stretching mechanism 40 includes three rotary rollers 41a, 41b and 41c arranged in order on the upper and lower sides of the absorbent sheet 105 at predetermined intervals d (refer to FIG. 3) in a second direction orthogonal to the direction of conveyance of the absorbent sheet 105, shown as arrow S.

On the other hand, a pair of holding rollers 45a and 45b are arranged outside of the rotary rollers 41b and 41c in the second direction.

The pair of holding rollers 45a and 45b hold both edges 105a and 105b extending in the length direction of the absorbent sheet 105. Moreover, the rotary rollers 41b and 41c press and bend the absorbent sheet 105 downwardly, whereas the rotary roller 41a presses and bends the absorbent sheet 105 upwardly.

With this, the absorbent sheet 105 is stretched in the second direction.

The position in which the rotary rollers 41a, 41b and 41c are arranged may be adjusted as appropriate in accordance with the strength of the absorbent sheet 105, weight of the crushed-pulp part, strength of tissue, etc., and is not limited particularly. If a force to be applied for stretch is too small, slits cannot be formed sufficiently, whereas if the force is too great, the absorbent sheet 105 itself can be broken.

The rotary rollers 41a, 41b and 41c are about 3 mm in thickness. Though the thickness can be set as appropriate, the thickness may be typically from 0.5 mm or more to 5 mm or less.

The rotary roller 41a is engaged with a rotation shaft 42 provided on the lower side of the absorbent sheet 105, and is a roller having a circular cross-section. With this, the rotary roller 41a is formed to be rotatable in association with the conveying speed of the absorbent sheet 105 with the rotation shaft 42 as an axis.

On the other hand, the rotary rollers 41b and 41c are engaged with a rotation shaft 43 provided on the upper side of the absorbent sheet 105, each being a roller having a cross-sectional shape obtained by cutting a circular arc of a predetermined angle from a circular shape. The length of each circular arc remaining without being cut substantially corresponds to the rotation-direction length of an area of the slitting roller 21 in which the slitting blades 22 are arranged.

A drive motor as rotary-roller drive mechanism, not shown, for rotating the rotary rollers 41b and 41c is connected to the rotary rollers. Referring to FIG. 4, rotation of the rotary rollers 41b and 41c is controlled by the drive motor so that when pressed parts 150 of the absorbent sheet 105 pass, arc portions 411b and 411c come to the side of the absorbent sheet 105, and when areas of the absorbent sheet 105 in which no pressed parts 150 are formed pass, cut portions 412b and 412c come to the side of the absorbent sheet 105.

In this embodiment, the drive motor is connected to the rotary rollers 41b and 41c, which is not limited particularly. Optionally, the drive motor may be connected to one of the rotary rollers, which has a sectional shape obtained by cutting the circular arc of the predetermined angle from a circular shape.

The pair of holding rollers 45a and 45b are connected to a drive motor as holding-roller drive mechanism, not shown, for rotating the holding rollers. In this embodiment, the drive motor is connected to all of the rollers constituting the pair of holding rollers 45a and 45b, which is not limited particularly.

Cutting Mechanism

Referring to FIG. 1, the cutting mechanism 30 includes a cutting roller 31, a drive motor as cutting-roller rotation mechanism, not shown, for rotating the cutting roller 31, and a receiving-side roller 35 arranged opposite the cutting roller 31 and cooperating with the cutting roller 31 to hold the absorbent sheet 105.

The cutting roller 31 has a cutting blade, not shown, having a cutting edge at a distal end. A sponge having higher reaction resilient force is partly or wholly arranged on the internal side of the cutting roller 31.

Rotation of the cutting roller 31 is controlled by the drive motor to form absorbent bodies 110A to D as will be described later. Specifically, the absorbent bodies 110A to D are configured so that an area in which no slits 155A to D are formed is arranged in a center portion in the length direction. Furthermore, areas in which slits 155A to D are formed are arranged at both sides of the center portion, i.e. the center portion is arranged between the areas which are formed slits.

The receiving-side roller 35 is pressed against the cutting roller 31 by a predetermined pressing force. The receiving-side roller 35 is not limited particularly, and may have a soft surface so as not to damage the cutting edge of the cutting blades. Moreover, the receiving-side roller 35 is rotated in synchronicity with the cutting roller 31 so as not to produce a shearing force in the cutting blades.

Operation of the Manufacturing Apparatus

The manufacturing apparatus 1 operates as follows.

The absorbent sheet 105 provided to the manufacturing apparatus 1 is first conveyed to the slitting mechanism 20 by the conveying mechanism.

The slitting roller 21 of the slitting mechanism 20 is rotated by the drive motor. With rotation of the slitting roller 21, the plurality of slitting blades 22 having cutting edges extending in the direction of rotation are pressed against the absorbent sheet 105, forming a plurality of pressed parts 150 that extend in the direction of conveyance.

Next, the absorbent sheet 105 in which the pressed parts 150 extending in the first direction are formed is conveyed to the stretching mechanism 40 by the conveying mechanism.

The pair of holding rollers 45a and 45b of the stretching mechanism 40 serve to pass the absorbent sheet 105 while holding both edges 105a and 105b in the length direction of the absorbent sheet 105.

The rotary roller 41a is freely rotated in association with the passing speed of the absorbent sheet 105 with the rotation shaft 42 as an axis. The passing absorbent sheet 105 is pressed and bent upwardly by the rotary roller 41a.

The rotary rollers 41b and 41c are rotated by the drive motor. By the drive motor, when the pressed part 150 of the absorbent sheet 105 passes, the arc portions 411b and 411c of the rotary rollers 41b and 41c come to the side of the absorbent sheet 105, so that the passing absorbent sheet 105 is pressed and bent downwardly by the arc portions 411b and 411c.

With this, the absorbent sheet 105 is stretched in the second direction to allow the slitting blades 22 to penetrate into the pressed part 150, forming the slits 155 into the pressed part 150.

On the other hand, when an area of the absorbent sheet 105 having no pressed part 150 formed therein passes, the cut portions 412b and 412c come to the side of the absorbent sheet 105, so that the rotary rollers 41b and 41c are separated from the passing absorbent sheet 105. Therefore, the absorbent sheet 105 is not pressed and bent downwardly, and thus is not reduced in bulk, resulting in no degradation in flexibility of the area of the absorbent sheet 105 having no pressed part 150 formed therein.

Next, the absorbent sheet 105 having slits 155 formed therein is conveyed to the cutting mechanism 30 by the conveying mechanism.

The cutting roller 31 of the cutting mechanism 30 is rotated by the drive motor. With rotation of the cutting roller 31, the cutting edge arranged projectively is pressed against the absorbent sheet 105. With this, the absorbent sheet 105 is cut in a predetermined shape such as a roughly rectangular shape, forming the absorbent body 110A to D used for absorbent articles such as sanitary napkins 100A to D.

Absorbent body

Figure 5:
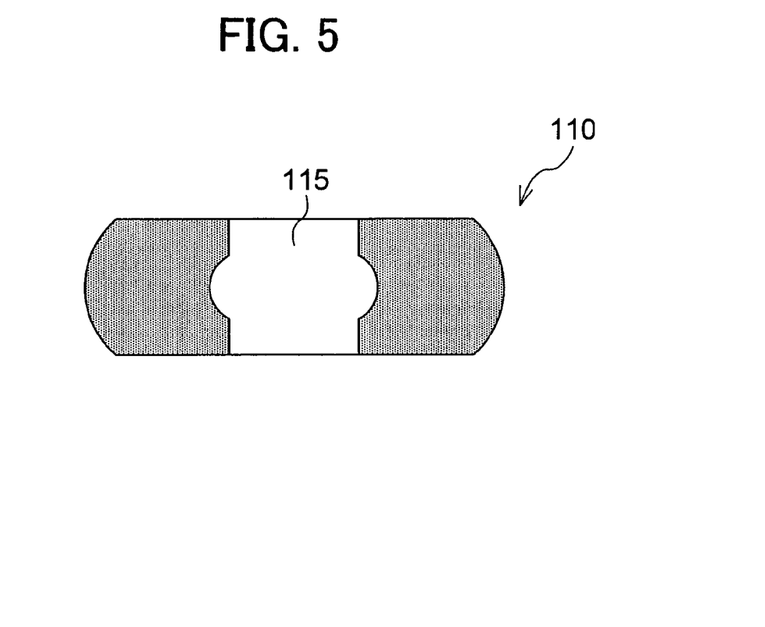
FIG. 5 is a plan view showing an absorbent body manufactured by the manufacturing apparatus according to the present embodiment.

FIG. 5 is a plan view showing an absorbent body 110 manufactured by the manufacturing apparatus 1 according to the embodiment. FIG. 6A to 6D are plan views showing sanitary napkins 100A to D using the absorbent bodies 110A to 110D with top sheets removed.

Figure 6A:
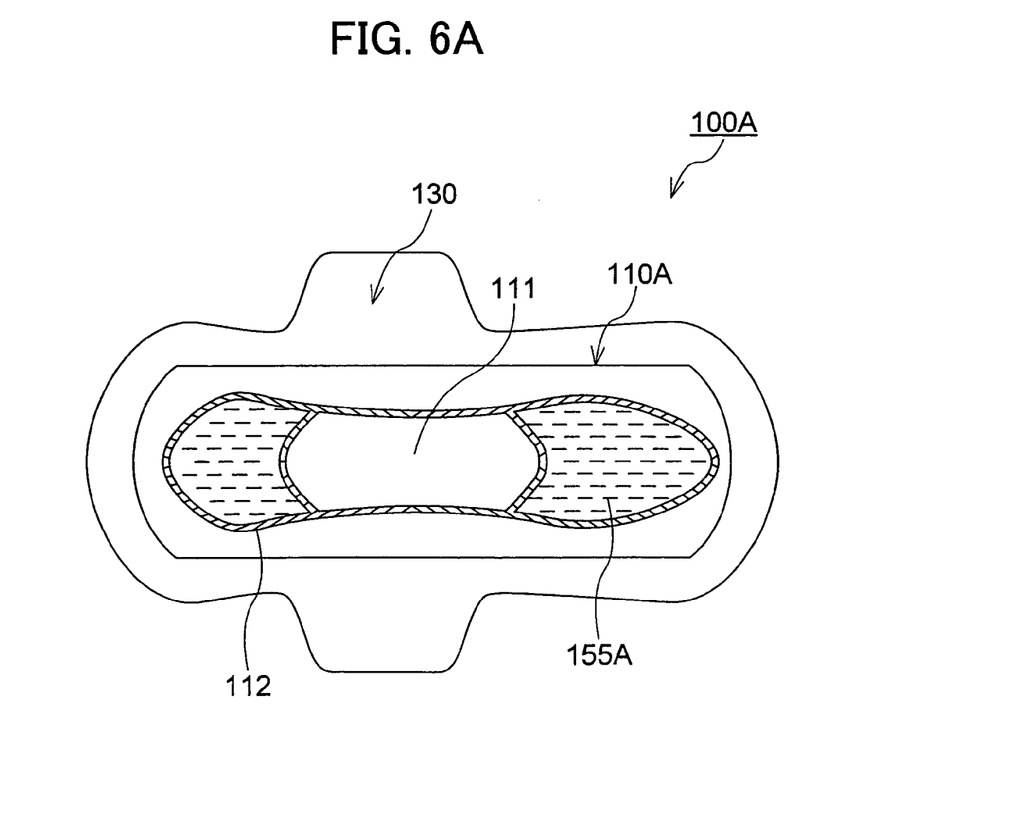
FIG. 6A to FIG. 6D are plan views showing absorbent articles using the absorbent bodies with top sheets removed.
Figure 6B:
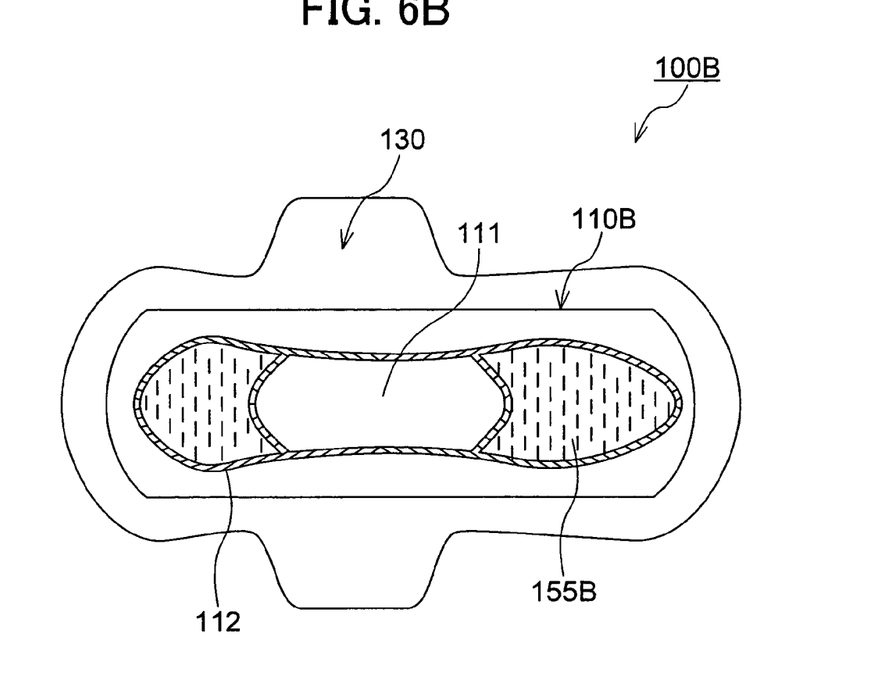
Figure 6C:
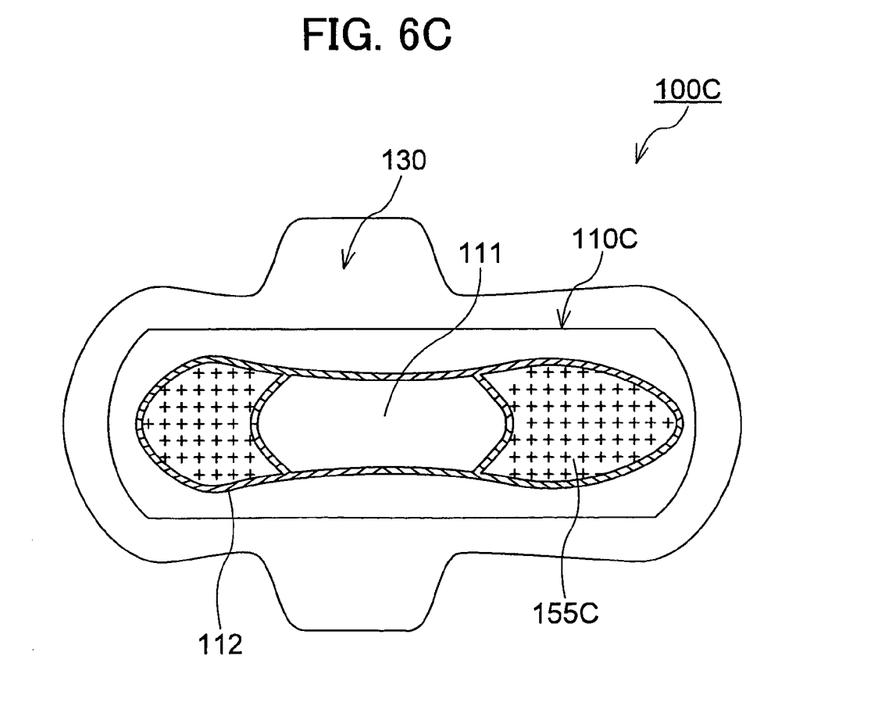
Figure 6D:
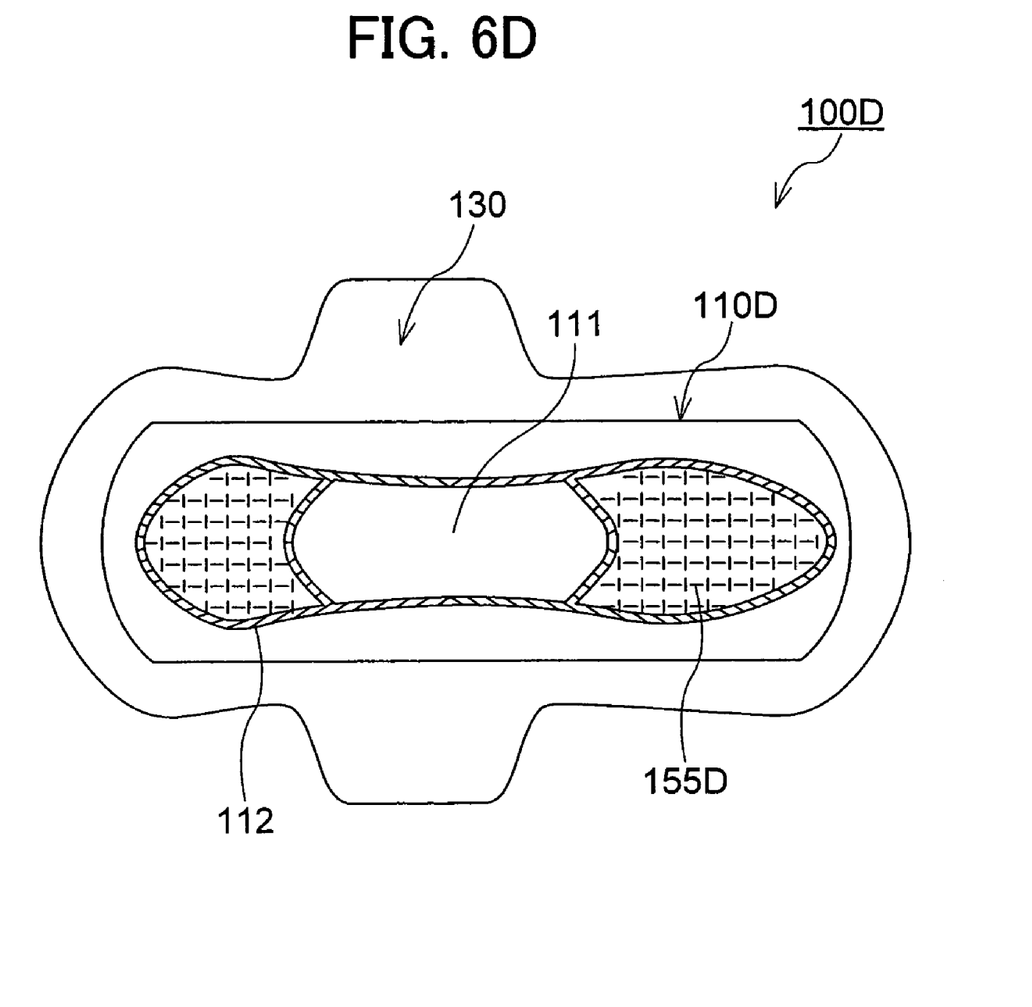

FIG. 6A shows examples of the sanitary napkin using the absorbent body manufactured by directing slitting blades which will be described later in the first direction, FIG. B shows the sanitary napkin using the absorbent body manufactured by directing the slitting blades in the second direction, FIG. 6C and 6D show the sanitary napkins using absorbent bodies manufactured by directing the slitting blades in the first direction and the second direction.

The absorbent bodies 110A to D are manufactured by the manufacturing apparatus 1 in a manner described above.

Referring to FIGS. 5 and 6A to D, the absorbent bodies 110 to 110D have roughly rectangular shapes, wherein the plurality of slits 155A to D extending along the length direction are provided, except in the 500 g/m$^2$ weight area (designated by reference 115 in FIG. 5) of the crushed-pulp part arranged in the center portion in the length direction of the absorbent body 110. Referring to FIG. 5, it is noted that the slits 155 are actually formed in areas 116, but the illustration thereof is omitted.

The absorbent body 110A serves as an absorbent body of the sanitary napkin 110A, for example.

Referring to FIG. 6A, the sanitary napkin 100 includes a liquid permeable top sheet, a liquid impermeable back sheet 130, and absorbent body 110A interposed therebetween. The absorbent body 110A is arranged so that a periphery of an area opposite a wearer's vaginal opening 111 corresponds to the 500 g/m$^2$ weight area of the crush-pulp part, whereas the plurality of slits 155 extending along the length direction is formed outside of the periphery of the opposite area 111.

Here, the word "opposite area" refers an area which is formed on the surface of the sanitary napkin, and the area which is opposite to a wearer's vaginal opening. The word "a periphery of the opposite area" refers the area which is a vicinity of the opposite area. That is, the areas numbered 111 in FIG. 6A to 6D include not only the opposite are but also the periphery (vicinity) of the opposite areas.

An embossed/compressed part 112 formed with the top sheet is provided to the absorbent body 110A so as to surround the areas in which the slits 155A are formed.

A pressure-sensitive adhesive layer as displacement preventing means, not shown, is arranged on the clothes-side surface of the back sheet 130.

With the sanitary napkin 100A, due to arrangement of the plurality of slits 155A, when clothes moves, the absorbent body 110A moves and bends together therewith, so that the projection-side external surface of a bend opens the slits 155A, whereas the inside of the bend closes the slits 155A. With this, the sanitary napkin 100A can deform, bend, etc., while restraining occurrence of a high-stiffness part at the bend, resulting in enhancement in flexibility.

Moreover, a problem in that the linkage between the absorbent body 110A and the back sheet 130 is degraded by a reduction in adhesion area therebetween, does not easily occur. Therefore, the back sheet 130 moves together with movement of the clothes through the pressure-sensitive adhesive layer, and the absorbent body 110A can deform in association with movement of the back sheet 130, resulting in restraint of twisting of the absorbent body 110A.

Further, due to arrangement of the plurality of slits 155A extending along the length direction, the absorbent body 110A moves together with movement of the clothes, and deforms and rises easily in the central portion of in the width direction, for example, making close contact with a wearer's gluteal cleft. Therefore, discharged bodily fluids can be restrained from leaking from the gluteal cleft.

Furthermore, since the absorbent body 110A is arranged so that the periphery of the area opposite a wearer's vaginal opening 111 corresponds to the 500 g/m$^2$ weight area of the crush-pulp part, the periphery of the opposite area 111 has a relatively high stiffness. Therefore, twisting of the absorbent body 110A due to excessive flexibility of the opposite area can be restrained.

The first embodiment produces the following working effects.

Since the slitting mechanism 20 is configured so that the slitting blades 22 extend in the first direction, the slitting blades 22 are pressed against the absorbent sheet 105, forming the pressed part 150 extending in the first direction.

The stretching mechanism 40 includes three rotary rollers 41*a*, 41*b* and 41*c* arranged in order on the upper and lower sides of the conveyed absorbent sheet 105 at a constant interval in the second direction. With this, when conveyed to pass through the stretching mechanism 40, the absorbent sheet 105, having pressed part 150 formed therein, is pressed and bent upwardly and downwardly in alternate order by the respective rotary rollers 41*a*, 41*b* and 41*c*, causing stretch in the second direction.

As a consequence, even if the slitting blades 22 are not sufficiently pressed against the absorbent sheet 105 conveyed at high speed to penetrate into the absorbent sheet 105, since the absorbent sheet 105 is stretched in the second direction, the slitting blades 22 penetrate into the pressed part extending in the first direction, forming the slits 155 into the pressed part.

Therefore, even when high-speed conveyance (100 to 400 m/min, for example) of the continuous absorbent sheet is performed, the absorbent body 110A having slits 155A formed therein can be manufactured more assuredly.

Second Embodiment

Figure 7:
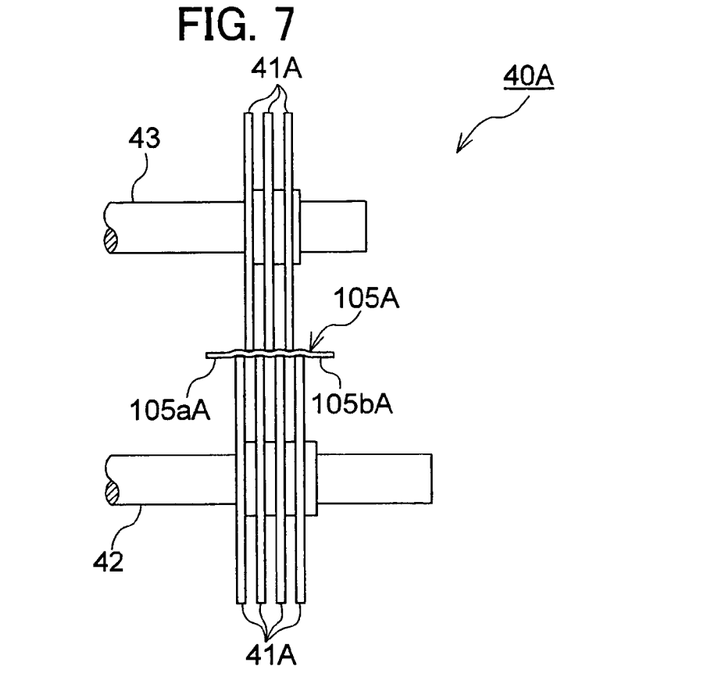
FIG. 7 is a view showing a stretching mechanism of a manufacturing apparatus according to a second embodiment of the present invention seen from the direction of rotation.

FIG. 7 is a view showing a stretching mechanism 40A of a manufacturing apparatus according to the second embodiment of the present invention seen from the direction of rotation.

The second embodiment differs from the first embodiment in the configuration of the stretching mechanism 40A.

Specifically, referring to FIG. 7, the stretching mechanism 40A includes seven rollers 41A arranged in order on the upper and lower sides of the absorbent sheet 105A at a constant interval in the second direction orthogonal to the direction of conveyance of an absorbent sheet 105A.

In this embodiment, the stretching mechanism 40A includes no rollers for holding both edges 105*a*A and 105*b*A arranged in the direction corresponding to the length direction of the absorbent sheet 105A. However, at high-speed conveyance, particularly, since a length-direction tension provided from the conveying mechanism to convey the absorbent sheet 105A is greater, stretch operation in the second direction of the absorbent sheet 105A by the stretching mechanism 40A is not degraded seriously.

Therefore, the second embodiment produces the same working effects as those of the first embodiment.

Third Embodiment

Figure 8:
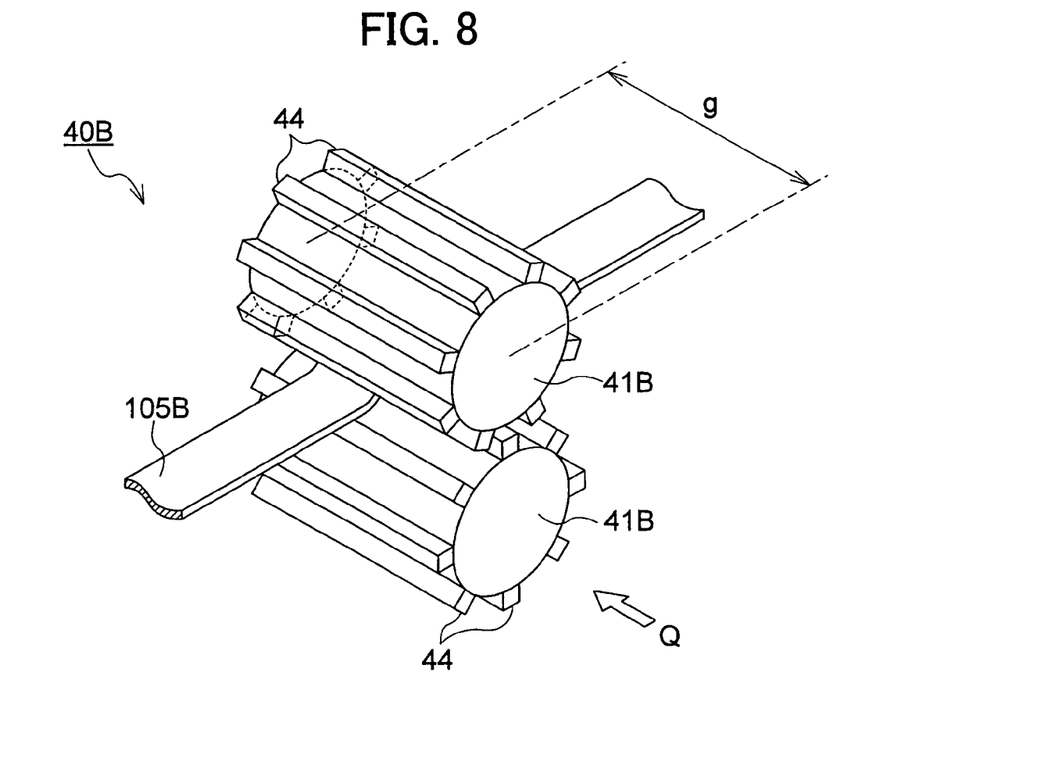
FIG. 8 is a perspective view showing a stretching mechanism of a manufacturing apparatus according to a third embodiment of the present invention.
Figure 9:
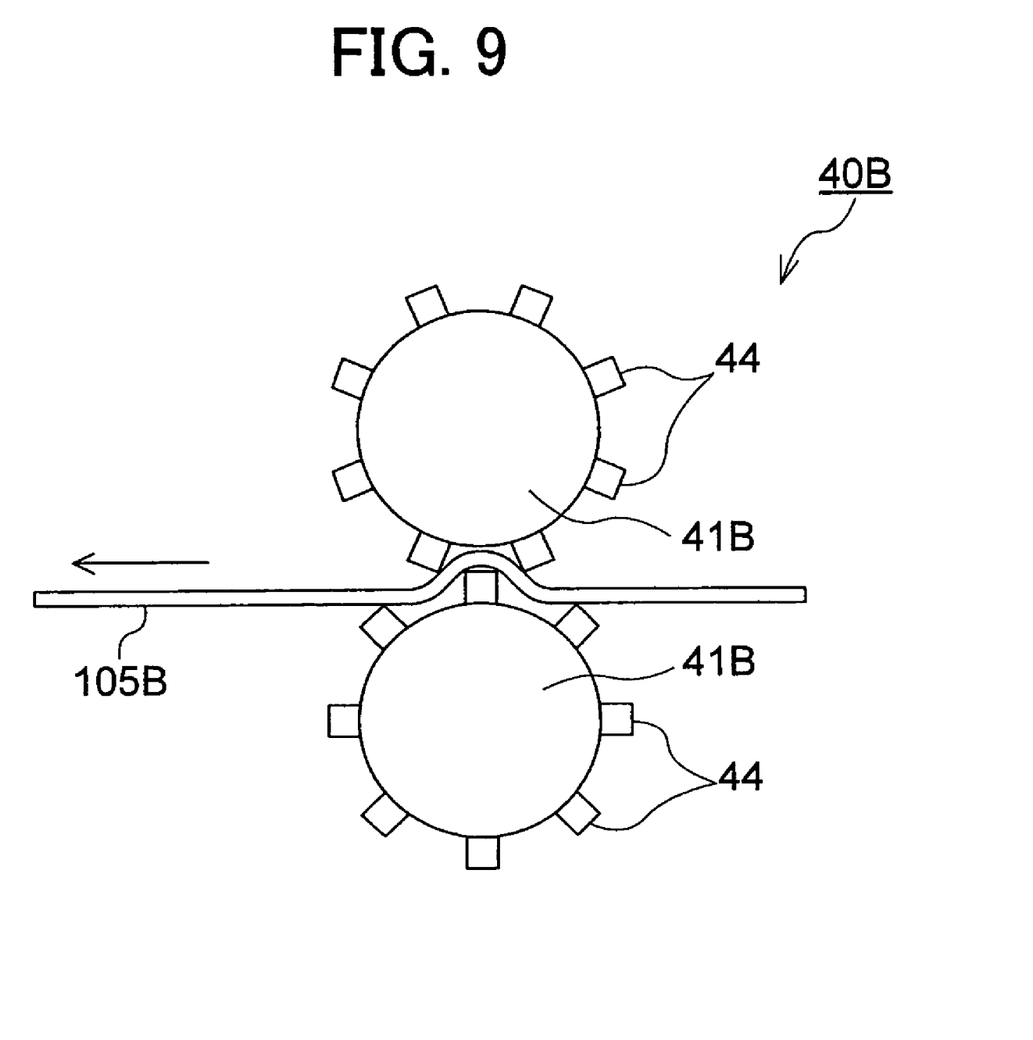
FIG. 9 is a view showing the stretching mechanism in FIG. 8 seen from the direction of an arrow Q.

FIG. 8 is a perspective view showing a stretching mechanism 40B of a manufacturing apparatus according to the third embodiment of the present invention. FIG. 9 is a view showing the stretching mechanism 40B in FIG. 8 seen from the direction of an arrow Q.

The third embodiment differs from the first embodiment in the configuration of the slitting mechanism and stretching mechanism 40B.

Specifically, the slitting roller constituting the slitting mechanism includes, on part of the external surface, a plurality of slitting blades. The slitting blades are arranged so that a cutting edge extends in the direction orthogonal to the direction of rotation of the slitting roller.

Referring to FIG. 8, the stretching mechanism 40B includes a pair of rotary rollers 41B each having on the external surface a plurality of projections 44 extending in the second direction orthogonal to the direction of conveyance. The pair of rotary rollers 41B have a width g greater than the width-direction dimension of an absorbent sheet 105B. With this, as the plurality of projections 44 of the pair of rotary rollers 41B engage with each other, the absorbent sheet 105B is engaged with the engaging part and is stretched in the direction of conveyance (the first direction).

The manufacturing apparatus operates as follows.

With rotation of the slitting roller, a plurality of slitting blades having cutting edges extending in the second direction orthogonal to the direction of rotation are pressed against the absorbent sheet 105B, forming a plurality of pressed parts extending in the second direction.

The absorbent sheet 105B in which the plurality of pressed parts extending in the second direction are formed is conveyed to the stretching mechanism 40B by the conveying mechanism.

When conveyed to pass through the stretching mechanism 40B, as the plurality of projections 44 of the pair of rotary rollers 41B extending in the second direction engage with each other, the absorbent sheet 105B, having pressed parts formed therein, is engaged with the engaging part. With this, the absorbent sheet 105B is stretched in the direction of conveyance to allow the slitting blades to penetrate into the pressed part extending in the second direction, forming the slits in the pressed part.

The absorbent body manufactured by the manufacturing apparatus according to this embodiment has a roughly rectangular shape, in which the plurality of slits extending along the width direction are arranged outside of the 500 g/m² weight area of the crushed-pulp part arranged in the center portion in the length direction of the absorbent body.

The absorbent body serves as an absorbent body of a sanitary napkin, for example.

The sanitary napkin includes a liquid permeable top sheet, a liquid impermeable back sheet, and absorbent body interposed therebetween. The absorbent body is arranged so that a periphery of an area opposite a wearer's vaginal opening corresponds to the 500 g/m² weight area of the crush-pulp part, wherein the plurality of slits extending along the width direction are formed outside of the periphery of the opposite area.

Typically, the crushed-pulp part constituting the absorbent body is often arranged in the length direction. In this case, since a value of flexural stiffness is higher in the length direction than in the width direction, the absorbent body may be bent in the width direction in a one-sided manner, leading to possible occurrence of twisting of the absorber. According to this sanitary napkin, however, since the plurality of slits extend in the width direction, the absorbent body is easily bent in the length direction as well. With this, the absorbent body can be bent in both the length and width directions, resulting in restraint of twisting of the absorbent body.

The third embodiment produces the following working effects.

Since the slitting mechanism is configured so that the slitting blades extend in the second direction orthogonal to the direction of conveyance, the slitting blades are pressed against the absorbent sheet 105B, forming the pressed part that extends in the second direction.

The stretching mechanism 40B includes pair of rotary rollers 41B each having, on the external surface, the plurality of projections 44 extending in the second direction. With this, when conveyed to pass through the stretching mechanism 40B, as the plurality of projections 44 extending in the second direction engage with each other, the absorbent sheet 105B, having pressed part formed therein, is engaged with the engaging part and is stretched in the direction parallel to the direction of conveyance (first direction).

As a consequence, even if the slitting blades are not sufficiently pressed against the absorbent sheet 105B conveyed at high speed to penetrate into the absorbent sheet 105B, since the absorbent sheet 105B is stretched in the first direction parallel to the direction of conveyance, the slitting blades penetrate into the pressed part extending in the second direction orthogonal to the direction of conveyance, forming the slits into the pressed part.

Therefore, even when high-speed conveyance (100 to 400 m/min, for example) of the continuous absorbent sheet is performed, the absorbent body having slits formed therein can be manufactured more surely.

While the preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

For example, in the embodiments, the extending direction of the cutting edges of the slitting blades 22 of the slitting mechanism 20 corresponds to the circumferential direction of the slitting roller 21 or the direction orthogonal thereto. This is not limitative, and the extending direction, shape, size, etc. of the slitting blades 22 may be set as appropriate in accordance with the purpose.

In addition, the slitting blades 22 may be provided such that the slitting blades 22 extend along both the first direction and the second direction. Stretching mechanisms may be provided so that the stretching mechanisms stretch the absorbent sheet in the fist and the second direction as well. The slitting mechanisms and the stretching mechanisms may be provided in the same way as described above. Since slits are formed in the two directions, more favorable conformity to movement of the clothes can be provided than that of the absorbent body manufactured with slits in the single direction.

EXAMPLE

In this example, the manufacturing apparatus 1 was configured as in the first embodiment, by which the absorbent body 110A was manufactured from the continuous absorbent sheet 105. Taking samples of a pressed absorbent sheet before provided to the manufacturing apparatus 1, an absorbent sheet immediately after passing through the slitting mechanism 20, and an absorbent sheet immediately after passing through the stretching mechanism 40, values of stiffness of the absorbent sheets were measured.

The manufacturing apparatus 1 was actuated at the conveying speed of 170 m/min.

Values of the absorbent sheets were measured by a method based on the Gurley bending resistance examination. The Gurley bending resistance test is a stiffness test method (Gurley method) for paper and paperboard by a loading bending method described in Paper and Pulp Test Method No. 40-83, published by Japan Technical Association of the Pulp and Paper Industry (Japan TAPPI).

As for the results of measurement of the values of stiffness, the pressed absorbent sheet was 293 mg, the absorbent sheet immediately after passing through the slitting mechanism 20 was 355 mg, and the absorbent sheet immediately after passing through the stretching mechanism 40 was 205 mg.

With this, it was revealed that the absorbent sheet after passing through the slitting mechanism 20 has an area into which the slitting blades 22 of the slitting mechanism 20 did not penetrate and thus increases in stiffness. On the other hand, it was revealed that, by passing through the stretching mechanism 40, the slits 155A are also formed in an area into which the slitting blades 22 did not penetrate and thus decrease in stiffness. It was also revealed that the absorbent sheet after passing through the stretching mechanism 40 is smaller in stiffness than the absorbent sheet before passing through the slitting mechanism 20.

Thus, it was revealed that, according to the manufacturing apparatus 1 in the example, even when high-speed conveyance of a continuous absorbent sheet is performed, the absorber having slits formed therein and providing smaller stiffness and excellent flexibility can be manufactured more assuredly.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An elongated absorbent body comprising:
a high stiffness portion provided exclusively in a center portion in the longitudinal direction of the absorbent body, which high stiffness portion extends in the longitudinal direction;
a plurality of slits exclusively at opposite end of the high stiffness portion in the longitudinal direction;
an embossed portion formed to surround a region where the plurality of slits are formed;
wherein each of the plurality of slits is a through hole extending from a surface to a back face of the absorbent body, formed by piercing a plurality of slitting blade in a thickness direction of the absorbent sheet in a state the absorbent sheet is stretched in a direction orthogonal to a direction of forming of slits, and
the plurality of the slits are disposed continuously with a predetermined interval therebetween.

2. The absorbent body according to claim 1,
wherein a basis weight of crush-pulp in the high stiffness portion is 500 g/m$^2$, and
the basis weight of crush-pulp in the both side ends in the longitudinal direction of the absorbent sheet is 180 g/m$^2$.

3. The absorbent body according to claim 1,
wherein the plurality of slits are formed in a first direction and a second direction which is orthogonal to the first direction.

4. The absorbent body according to claim 3,
wherein the plurality of slits formed in the first direction and the second direction intersect each other.

5. A sanitary napkin comprising:
a liquid permeable top sheet;
a liquid impermeable back sheet; and
an elongated absorbent body interposed therebetween,
wherein the absorbent body includes:
a high stiffness portion provided exclusively in a center portion in the longitudinal direction of the absorbent body, which high stiffness portion extends in the longitudinal direction;
a plurality of slits exclusively at opposite ends of the high stiffness portion in the longitudinal direction,
an embossed portion in which the top sheet and a portion of the absorbent body are embossed so as to surround a region where the plurality of slits are formed,
wherein each of the plurality of slits is a through hole extending from a surface to a back face of the absorbent body, formed by piercing a plurality of slitting blade in a thickness direction of the absorbent sheet in a state the absorbent sheet is stretched in a direction orthogonal to a direction of forming of slits, and
the plurality of slits are disposed continuously with a predetermined interval therebetween along the longitudinal direction of the absorbent body.

6. The sanitary napkin according to claim 5,
further comprising a plurality of slits formed along a width direction of the absorbent body.

7. The sanitary napkin according to claim 6,
the plurality of slits formed along the longitudinal direction and the width direction intersect each other.

8. A sanitary napkin comprising:
a liquid permeable top sheet;
a liquid impermeable back sheet; and
an elongated absorbent body interposed therebetween,
wherein the absorbent body includes:
a high stiffness portion provided in a center portion in the longitudinal direction of the absorbent body, which high stiffness portion extends in the longitudinal direction;
an absorbent sheet provided with a plurality of slits at both side ends in the longitudinal direction,
wherein the plurality of slits are through holes formed by piercing a plurality of slitting blade in a thickness direction of the absorbent sheet in a state the absorbent sheet is stretched in a direction orthogonal to a direction of forming of slits, and
the plurality of slits are disposed continuously with a predetermined intervals therebetween along a width direction of the absorbent body.

* * * * *